United States Patent [19]

Tennant

[11] 4,403,353

[45] Sep. 13, 1983

[54] ANTERIOR CHAMBER IMPLANT LENS

[76] Inventor: Jerald L. Tennant, 806 Greentree La., Duncanville, Tex. 75116

[21] Appl. No.: 277,250

[22] Filed: Jun. 25, 1981

[51] Int. Cl.$^3$ ............................ A61F 1/16; A61F 1/24
[52] U.S. Cl. ......................................................... 3/13
[58] Field of Search ........................................ 3/13, 1

[56] References Cited

U.S. PATENT DOCUMENTS

| | | | |
|---|---|---|---|
| 2,834,023 | 5/1958 | Lieb | 3/1 |
| 3,673,616 | 7/1972 | Fedorov et al. | 3/13 |
| 3,711,870 | 1/1973 | Deitrick | 3/13 |
| 3,866,249 | 2/1975 | Flom | 3/13 |
| 3,906,551 | 9/1975 | Otter | 3/13 |
| 3,913,148 | 10/1975 | Potthast | 3/13 |
| 3,922,728 | 12/1975 | Krasnov | 3/13 |
| 3,925,825 | 12/1975 | Richards et al. | 3/13 |
| 3,961,379 | 6/1976 | Highgate | 3/13 |
| 3,971,073 | 7/1976 | Richards et al. | 3/13 |
| 3,975,779 | 8/1976 | Richards et al. | 3/13 |
| 3,979,780 | 9/1976 | Boniuk | 3/13 |
| 3,986,214 | 10/1976 | Krasnov | 3/13 |
| 3,992,563 | 11/1976 | Tanaka | 526/219 |
| 3,994,027 | 11/1976 | Jensen et al. | 3/13 |
| 3,996,626 | 12/1976 | Richards et al. | 3/13 |
| 4,014,049 | 3/1977 | Richards et al. | 3/13 |
| 4,056,855 | 11/1977 | Kelman | 3/13 |
| 4,073,014 | 2/1978 | Poler | 3/13 |
| 4,085,467 | 4/1978 | Rainin et al. | 3/13 |
| 4,087,866 | 5/1978 | Choyce et al. | 3/13 |
| 4,092,743 | 6/1978 | Kelman | 3/13 |
| 4,110,848 | 9/1978 | Jensen | 3/13 |
| 4,127,903 | 12/1978 | Schachar | 3/13 |
| 4,159,546 | 7/1979 | Shearing | 3/13 |
| 4,174,543 | 11/1979 | Kelman | 3/13 |
| 4,242,760 | 1/1981 | Rainin | 3/13 |
| 4,249,271 | 2/1981 | Poler | 3/13 |
| 4,253,200 | 3/1981 | Kelman | 3/13 |
| 4,254,510 | 3/1981 | Tennant | 3/13 |
| 4,277,852 | 7/1981 | Poler | 3/13 |

FOREIGN PATENT DOCUMENTS

| | | | |
|---|---|---|---|
| 959314 | 3/1957 | Fed. Rep. of Germany | 3/13 |
| 1034325 | 7/1958 | Fed. Rep. of Germany | 3/13 |
| 1103399 | 11/1955 | France | 3/13 |
| 563174 | 7/1977 | U.S.S.R. | 3/13 |

OTHER PUBLICATIONS

"A Lens for All Seasons", Tennant, Jerald L., 1976.
"The Evolution of the Anterior Chamber Implant Up To and Including the Choyce MK IX", Choyce, D. P., paper presented at the 83rd Annual Meeting of the American Academy of Ophthalmology, Oct. 26, 1978.
"The Mark VI, Mark VII and Mark VIII Choyce Anterior Chamber Implants", Proceedings of the Royal Society of Medicine, vol. 58, Sep. 1965, pp. 729-731, by Peter Choyce.
"The Intraocular Implant Lens Development and Results With Special Reference to the Binkhorst Lens", Nordlohne, Eugene Marcel, Published by the Williams and Wilkins Company, Copyright 1975, p. 16.
Rayner & Keeler Ltd. Lenses for Catalogue Numbers 456 and 469.
"Experience with Twelve Cases of Intra-ocular Anterior Chamber Implants for Aphakia", J. Boberg-Ans, British Journal of Opthalmology, vol. 45, No. 1, Jan. 1961, pp. 37-43.

Primary Examiner—Ronald L. Frinks
Attorney, Agent, or Firm—Richards, Harris & Medlock

[57] ABSTRACT

An intraocular implant unit (20) having a lens optic (22) and a limb (24) integral with the lens optic (22) extending outward radially from a first margin portion of the lens optic (22). An arcuate rim (26) is centered on the end of the limb (24) and a flexible support strand (28) is rooted in a second margin portion of the lens optic (22). Flexible support strand (28) is capable of adjusting to various sized anterior chambers such that the intraocular implant unit (20) can be utilized with various sized anterior chamber diameters.

8 Claims, 10 Drawing Figures

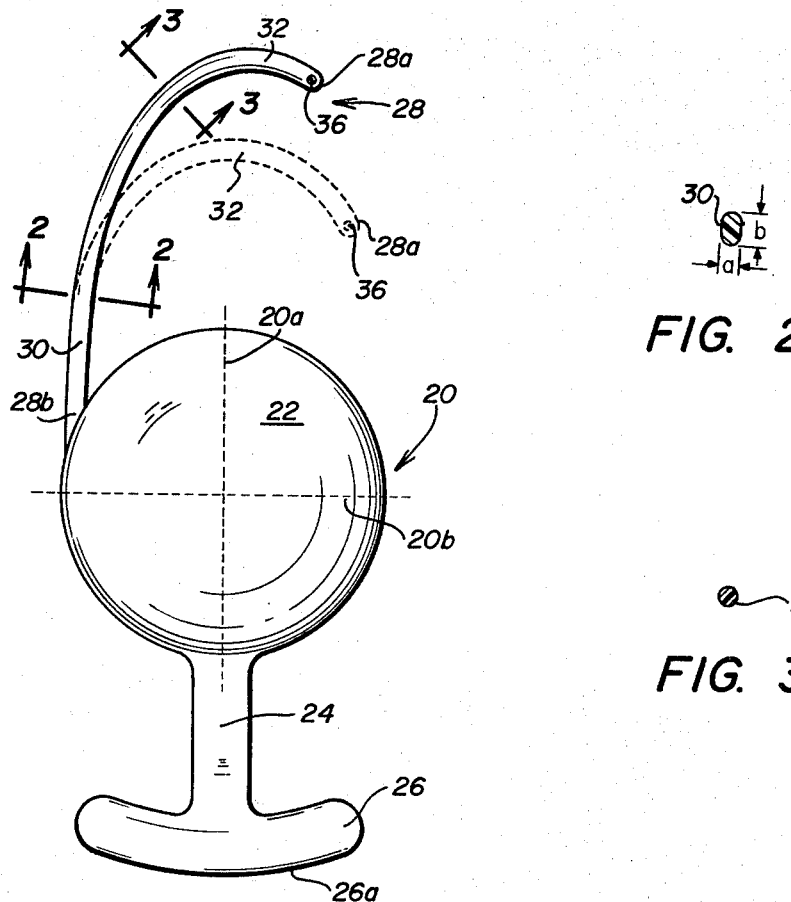
FIG. 1
FIG. 2
FIG. 3
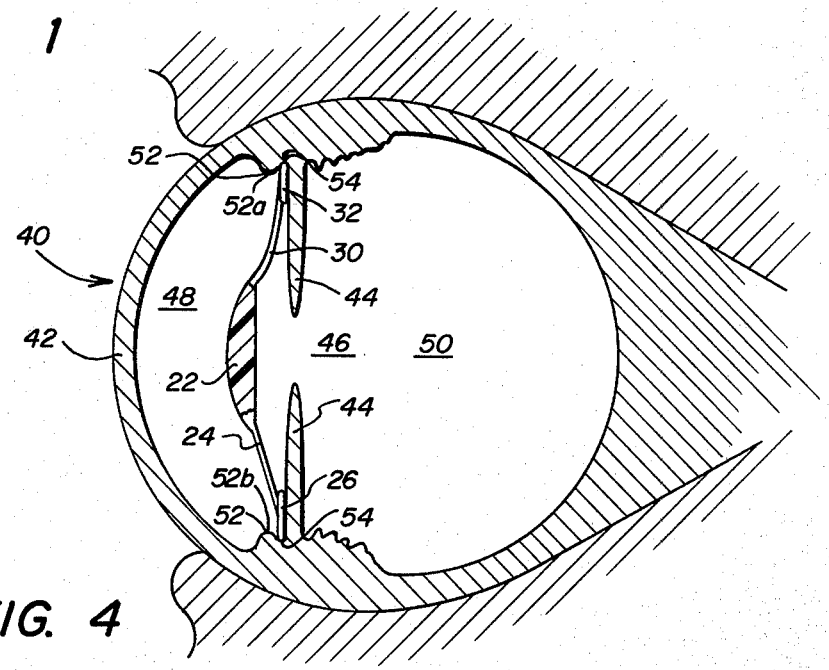
FIG. 4

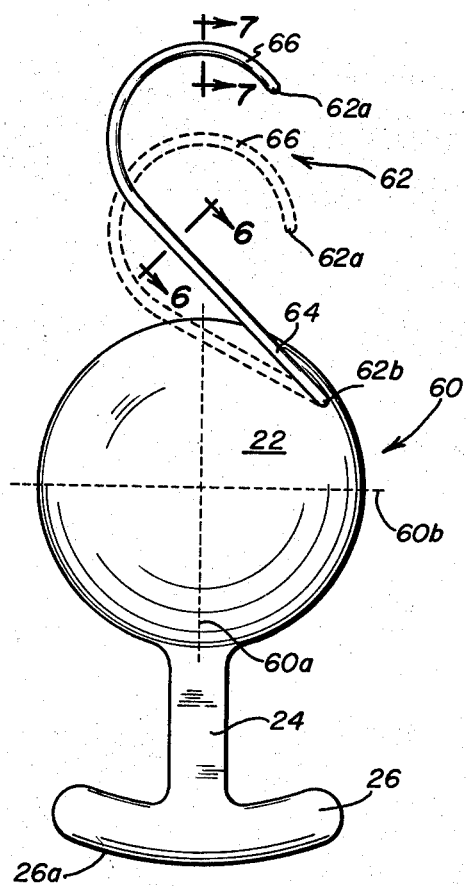
FIG. 5
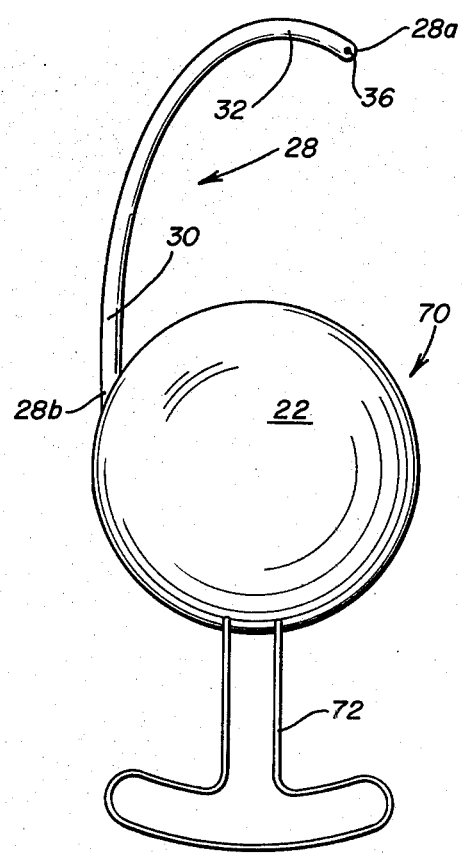
FIG. 8
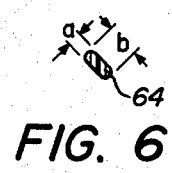
FIG. 6
FIG. 7
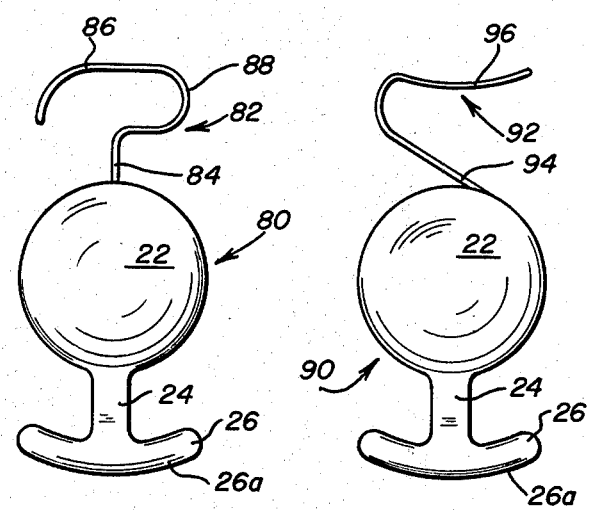
FIG. 9
FIG. 10

ANTERIOR CHAMBER IMPLANT LENS

TECHNICAL FIELD

This invention relates to intraocular implant lenses, and more particularly to a lens of light weight, shaped for a predetermined implant location in the anterior chamber of the eye and which is capable of adjusting to various sized anterior chamber diameters.

BACKGROUND ART

The history of intraocular lens implants can be traced to the method of fixation. Initially, intraocular lens implants were of the posterior chamber type developed by Harold Ridley. However, the technical difficulties and complications associated with the Ridley lens lead to a change in the positioning of the artificial lens in the eye. This change resulted in intraocular lenses being placed in the anterior chamber of the eye.

The evolution of anterior chamber lenses developed along two types. The first type is represented by the flexible loop lenses of the Dannheim lens illustrated in West German Pat. No. 1034325 issued to H. Dannheim on July 17, 1958 and entitled "Artificial Eye Lens". The second type of anterior lenses is represented by the Strampelli lens which is of a rigid type in the form of a meniscus ending in a dove tail.

The evolution of the Strampelli lens has resulted in the development of the Tennant lens illustrated in U.S. Pat. No. 4,261,065 issued to J. Tennant on Apr. 14, 1981 and entitled "Artificial Intraocular Lens with Forward-Position Optics". The evolution of the Dannheim lens has resulted in a semi-flexible lens that retains three or four points of fixation represented by the Kelman lens illustrated in U.S. Pat. No. 4,174,543 issued to C. Kelman on Nov. 20, 1979 and entitled "Intraocular Lenses". Futher development of the Dannheim and Kelman type flexible lenses has resulted in a semi-flexible lens with biarcuate fixation in which the fixating members match the curvature of the tissue in which they are affixed. Such a lens is described in U.S. Pat. No. 4,254,510 issued to J. Tennant on Mar. 10, 1981 and entitled "Implant Lens with Biarcuate Fixation".

Although the development of anterior chamber lenses has significantly progressed from the Dannheim and Strampelli types, it has still been found that the most common difficulty with anterior chamber lenses is the necessity to maintain an inventory of various sizes to fit various size eyes and more particularly the diameter of the anterior chamber of the recipient's eyes. In addition, a surgical judgment must be made on the part of the surgeon in determining the size of the anterior chamber in selecting the proper sized lens. An additional problem associated with anterior chamber lenses is that, although flexible lenses have been developed, such lenses do not have the desired ability to maintain lens stability necessary for the lens to be tolerated without destruction of the eye.

The effort for a flexible yet stable lens has its development in the Dannheim lens in which the loops were made of nylon. However, it has been found that these nylon loops dissolved and were unstable, even when freshly implanted, allowing the optic to move readily, forward, backward, or horizontally in the anterior chamber. Material such as polypropylene has been utilized in place of nylon; however, although being less likely to dissolve, polypropylene loops suffered in that such loops caused the position of the optic to be unpredictable and unstable.

Lens fixation loops have also been composed of polymethylmethacrylate (PMMA) material which material is unlikely to dissolve with improved stability over nylon and polypropylene type materials. However, lenses utilizing PMMA for such loops have been shown to be easily distorted which allow these loops to be pressed back out of the angle in which they are intended to reside which causes undesirable iris tucking and increased pressure within the anterior chamber of the eye. It thus has been found that the design of the anterior chamber lens loop fixation members is highly critical to the design of such lenses as these loops engage the anterior chamber tissue such that the centration and stability of the optic is dependent upon the integrity of these fixation loops.

A need has thus arisen for an anterior chamber lens having improved stability within the anterior chamber of the eye to prevent anterior-posterior movement of the optic, torsional movement and posterior migration of the lens within the anterior chamber of the eye. Furthermore, a need has developed for an anterior chamber lens which is flexible to fit within a range of diameters of the anterior chamber of the recipient eye while maintaining its stability and centration.

DISCLOSURE OF THE INVENTION

In accordance with the present invention, an anterior chamber lens is provided for substantially eliminating the problems heretofore associated with anterior chamber lenses, particularly providing for a flexible lens for insertion in various sized anterior chambers and which is position stable.

In accordance with the present invention, an intraocular implant lens unit for installation and immobilization in the anterior chamber of an eye of a patient is provided. The implant unit includes a lens and a limb integral with and extending outward radially from a margin portion of the lens. The unit further includes an arcuate rim centered on the end of the limb, the rim conforming to a circle having a diameter substantially equal to the diameter of the anterior chamber. Further provided is a flexible support strand having a first end connected to the lens and a second end. The first and second ends define a length therebetween. The flexible support strand is disposed approximately opposite the limb and is flexible to vary the length between the first and second ends. The flexible support strand engages the upper scleral spur of the patient's eye and adjusts the implant unit to the size of the anterior chamber to thereby immobilize the implant unit in the anterior chamber.

In accordance with another aspect of the present invention, an intraocular implant lens unit is provided and includes a central lens having a planar posterior surface and a convex anterior surface. A limb is provided and extends outwardly radially from a margin portion of the lens. An arcuate rim portion is centered on the end of the limb. The implant lens unit further includes a flexible strand having a first end connected to the central lens and a second end. The first and second ends define a length therebetween. The limb and the flexible strand both extend posterior of the posterior surface of the central lens as well as outwardly for facilitating support of the central lens in the scleral spur of an eye. The flexible strand is flexible to vary the length to adjust the intraocular implant lens unit to the size of the anterior chamber and thereby immobilize the intraocular implant lens unit in variable sized anterior chambers.

BRIEF DESCRIPTION OF DRAWINGS

For a more complete understanding of the present invention and for further advantages thereof, reference is now made to the following Detailed Description taken in conjunction with the accompanying Drawings in which:

FIG. 1 is a front view of an anterior chamber lens of the present invention;

FIG. 2 is a cross-sectional view taken generally along sectional lines 2—2 of the anterior chamber lens illustrated in FIG. 1;

FIG. 3 is a cross-sectional view taken generally along sectional lines 3—3 of the anterior chamber lens illustrated in FIG. 1;

FIG. 4 illustrates the anterior chamber lens of FIG. 1 implanted in the anterior chamber of an eye;

FIG. 5 is a front view of a second embodiment of an anterior chamber lens of the present invention;

FIG. 6 is a cross-sectional view taken generally along sectional lines 6—6 of the anterior chamber lens illustrated in FIG. 5;

FIG. 7 is a cross-sectional view taken generally along sectional lines 7—7 of the anterior chamber lens illustrated in FIG. 5;

FIG. 8 is a front view of a third embodiment of an anterior chamber lens of the present invention;

FIG. 9 is a front view of a fourth embodiment of an anterior chamber lens of the present invention; and FIG. 10 is a front view of a fifth embodiment of an anterior chamber lens of the present invention.

DETAILED DESCRIPTION

Referring to FIG. 1, an intraocular implant lens of the present invention is illustrated and is generally identified by the numeral 20. Lens 20 includes a lens optic 22 of plano-convex shape which is formed integrally with a 6-o'clock substantially rigid limb 24. Limb 24 extends diametrically from one edge of lens optic 22. An arcuate rim segment 26 is integral with and centered on the end of limb 24 opposite lens optic 22. Rim segment 26 spans an arc of about 6 to 8 millimeters and is of generally the same thickness and width of limb 24, about 1.2 millimeters. Rim segment 26 lies in a plane perpendicular to an axis 20a of lens 20 and presents a curved outer surface 26a which is preferably rounded on the edges and smooth to provide contact over the entire length of surface 26a with the lower scleral spur in the anterior chamber of an eye into which lens 20 is to be implanted. Rim segment 26 circumscribes a circular arc of about 60° extend and has a common center located at about the center of lens optic 22.

Integrally formed with lens optic 22 of lens 20 is a flexible support strand, generally identified by the numeral 28 having ends 28a and 28b. The straight line distance between ends 28a and 28b is defined herein as a chord length. Flexible support strand 28 includes a stem portion 30 integral with lens optic 22 and an arcuate portion 32 having free end 28a. Arcuate portion 32 is positioned within the anterior chamber of an eye such that arcuate portion 32 engages the upper scleral spur of the anterior chamber. It can be seen that flexible support strand 28 has a generally parabolic configuration such that flexible support strand 28 assumes the same curvature of the tissue of the eye of the upper portion of the anterior chamber to eliminate points of pressure between lens 20 and the eye.

An important aspect of the present invention is the adjustability of lens 20 such that lens 20 can be utilized in various sized eyes. Flexible support strand 28 of the present lens 20 has the ability to flex between a range of positions. As illustrated in FIG. 1, flexible support strand 28 can assume a range of positions from the position indicated in solid lines to the position indicated in dotted lines. This range of positions permits the overall size of lens 20 to change to exactly conform to the diameter of the anterior chamber of an eye. In the dotted line position the chord length of flexible support strand 28 is less than the chord length in the solid line position. It can be seen that the chord length varies depending on the diameter of the anterior chamber.

Typically, lens 20 would fit a range of anterior chambers having a diameter from approximately 12.0 millimeters as illustrated in the dotted line position of flexible support strand 28 through anterior chambers having a diameter of approximately 13.5 millimeters as illustrated in the solid line position of flexible support strand 28 shown in FIG. 1. This adjustable nature of lens 20, provided by flexible support strand 28, eliminates the necessity to maintain an inventory of various sized anterior chamber lenses as well as eliminates the necessity of critical surgical measurements and judgments in deciding the proper sized lens for implantation.

In a typical embodiment, lens optic 22 would have a diameter of approximately 4 to 6 millimeters. The chord length of rim segment 26 would be approximately 6 to 8 millimeters as would the diameter of arcuate portion 32 of flexible support strand 28. Typically, the radius of the outer surface 26a of rim segment 26 measured from the center of lens optic 22 would be of the order of about 6 to 7 millimeters as would be the distance from the center of lens optic 22 to arcuate portion 32 of flexible support strand 28 measured along axis 20a, such that the maximum distance between arcuate portion 32 of flexible support strand 28 and the outer surface 26a of rim segment 26 approximates the diameter of the anterior chamber of an eye.

The lens 20 of the present invention as illustrated in FIG. 1, provides fixation which prevents rotation of lens optic 22 within the eye of a patient. Limb 24 of intraocular implant lens 20 dictates vertical centration of lens optic 22. Arcuate rim segment 26 prevents horizontal displacement while spreading the weight of lens 20 over a large weight-bearing surface. Additionally, limb 24 and rim segment 26 prevent torsional movement of lens 20 with posterior migration.

Referring simultaneously to FIGS. 1, 2 and 3, FIG. 2 illustrates the cross-sectional area of stem portion 30 of flexible support strand 28 as being substantially rectangular while FIG. 3 illustrates the cross-sectional area of arcuate portion 32 of flexible support strand 28 as being substantially circular in shape. The length "a" (FIG. 2) of stem portion 30 is approximately 0.25 millimeters. The length "b" of stem portion 30 is approximately 0.5 millimeters. The diameter of arcuate portion 32 is approximately 0.25 millimeters. This configuration constrains the flexion of flexible support strand 28 to occur only in an axis that is parallel with lens optic 22, thereby inhibiting anterior or posterior movement of intraocular implant lens 20 within the anterior chamber of an eye.

Disposed at end 28a of flexible support strand 28 is an aperture 36. Aperture 36 can be utilized by the surgeon with a suitable instrument to center and position lens 20 during implantation.

Referring to FIG. 4, the present lens 20 is shown implanted in an eyeball 40. Eyeball 40 includes a cornea 42 and an iris 44 having a central opening or pupil 46. Iris 44 divides eyeball 40 into an anterior chamber 48 and a posterior chamber 50. A scleral spur 52 in anterior chamber 48 is spaced from iris 44 thereby defining a groove 54. Scleral spur 52 has an upper portion 52a and a lower portion 52b. Lens 20 is shown in position in anterior chamber 48 of eyeball 40 such that rim segment 26 lies within groove 54 adjacent lower scleral spur 52b, and such that arcuate portion 32 of flexible support strand 28 lies within groove 54 adjacent upper scleral spur 52a.

While the lens 20 has been shown as having a plano-convex configuration (FIGS. 1 and 4) it will be understood that lens 20 may be made convex-plano or biconvex. However, the plano-convex configuration is preferred inasmuch as it provides maximum spacing between the iris and the posterior surface of the lens. Irritation in the postoperative period of the raw edges of the iris is thus avoided.

Optic 22, limb 24, rim segment 26 and support strand 28 are all made of material suitable for eye implantation. Such material in the preferred embodiment of the present invention comprises polymethylmethacrylate (PMMA). Alternatively, limb 24 may be of a softer material of the nature of hydrogels (PHEMA).

Thus from the foregoing, it will be seen that intraocular implant lens 20 is provided, comprising a lens optic 22 with a support strand 28 and a limb 24 supporting rim segment 26. Arcuate rim segment 26 has its center of curvature at the center of lens optic 22 and is disposed from the center of lens optic 22 about one-half the diameter of the anterior chamber 48 in which lens 20 is to be implanted. The overall length of lens 20 approximates the diameter of anterior chamber 48 due to the adjustable nature of flexible support strand 28 which flexes between a range of positions as shown in FIG. 1 to adjust to various sized anterior chambers of an eye.

Referring now to FIG. 5, a second embodiment of the present intraocular implant lens is illustrated and is generally identified by the numeral 60. Like numerals are utilized in FIG. 5 for like and corresponding components previously identified with respect to lens 20. Lens 60 includes a flexible support strant generally identified by the numeral 62 having ends 62a and 62b defining a chord length therebetween. Flexible support strand 62 includes a stem portion 64 and an arcuate portion 66. Flexible support strand 62 is integral with lens optic 22 and connects to the side opposite that shown in FIG. 1 with respect to lens 20. Stem portion 64 of flexible support strand 62 interconnects to lens optic 22 of lens 60 at approximately a 45° angle with respect to an axis 60b of lens 60. In this configuration, vertical forces applied to arcuate portion 66 of flexible support strand 62 are directed along an axis 60a of lens 60 whereas such forces are directed to the 10-o'clock position of lens 20 (FIG. 1). The positioning of flexible support strand 62 permits flexion of arcuate portion 66 in addition to stem portion 64.

As illustrated in FIG. 5, flexible support strand 62 is capable of adjusting to the diameter of the anterior chamber of an eye in a similar manner as described with respect to flexible support strand 28 (FIG. 1). Flexible support strand 62 is capable of adjusting from the position illustrated in the solid lines to the position illustrated in the dotted lines to adjust lens 60 for anterior chamber diameters from approximately 13.5 millimeters to approximately 12.0 millimeters. In this manner, lens 60 can be utilized for implantation in various sized anterior chambers.

FIGS. 6 and 7 illustrate cross-sectional areas of flexible support strand 62 which is configured in a similar manner to flexible support strand 28 as illustrated in FIGS. 2 and 3.

Referring to FIG. 8, wherein like numerals are utilized for like and corresponding components previously identified, a further embodiment of the present intraocular implant lens is illustrated and is generally identified by the numeral 70. Lens 70 includes lens optic 22 and flexible support strand 28 as previously described with reference to FIG. 1. Substituted in lens 70 for limb 24 and rim segment 26, which were solid and integral with lens optic 22 of lens 20, is a continuous loop 72 in a same generally shape of limb 24 and rim segment 26 of lens 20. Loop 72 may be composed of extruded PMMA or similar materials, and is rooted to optic 22 in approximately the 6-o'clock position. Loop 72 creates a fenestration for decreasing the weight of lens 70.

Referring now to FIG. 9, wherein like numerals are utilized for like and corresponding components previously identified, a fourth embodiment of the present intraocular implant lens is illuatrated and is generally identified by the numeral 80. Lens 80 includes a flexible support strand generally identified by the numeral 82. Flexible support strand 82 incudes a stem portion 84 interconnected to lens optic 22 in the 12-o'clock position and an arcuate portion 86. Arcuate portion 86 includes a doubly folded portion 88. Arcuate portion 86 flexes in a manner similar to arcuate portion 32 (FIG. 1) and arcuate portion 66 (FIG. 5) to permit lens 80 to be utilized in various sized anterior chambers.

FIG. 10 illustrates a fifth embodiment of the present intraocular implant lens, wherein like numerals are utilized for like and corresponding components previously identified, which is generally identified by the numeral 90. Lens 90 includes a flexible support strand generally identified by the numeral 92. Flexible support strand 92 includes a stem portion 94 and an arcuate portion 96. Stem portion 94 is interconnected to optic 22 at approximately a 45° angle with respect to an axis 90b of lens 90. Arcuate portion 96 of flexible support strand 92 is capable of flexing in a manner similar to arcuate portion 66 of flexible support strand 62 (FIG. 5) to adjust for various sized anterior chambers.

Therefore, it can be seen that the present intraocular implant lens utilizing a flexible support strand as a fixation element is capable of implantation into various sized anterior chambers thereby eliminating the need for an inventory of various sized lenses and eliminating the critical nature of surgical measurement and selection of properly sized anterior chamber lenses. Furthermore, the fixation members of the present intraocular implant lens are shaped to match the scleral spur diameter of the anterior chamber such that the lens is immobilized within the anterior chamber with minimal anterior-posterior movement of the optic, and minimal torsional movement.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An intraocular implant unit for installation and immobilization in a circularly bounded chamber of an eye of a patient comprising:
a lens disposed in a first plane for insertion within the chamber of the eye;
a limb integral with and extending outward from a margin portion of said lens to a second plane for placement within the chamber of the eye, said second plane being spaced apart from said first plane;
means extending from said limb and lying in said second plane for engaging a first portion of the chamber to thereby minimize torsional movement of said lens in the chamber;
a flexible strand having a first end connected to said lens in said first plane and a second end lying in said second plane; and
an elongated arcuate portion extending from said flexible strand second end and lying in said second plane for engaging a second portion of the chamber approximately opposite said first portion of the chamber, said elongated arcuate portion being disposed approximately opposite said means extending from said limb, and said flexible strand being doubly folded in a third plane approximately common to said first end of said flexible strand and to the ends of said elongated portion to flex in said third plane between said flexible strand first end and said elongated arcuate portion for varying the distance between said lens and said elongated arcuate portion, such that said elongated arcuate portion may engage said second portion of the chamber, said doubly folded portion not being engageable with eye tissue defining the chamber to thereby adjust the intraocular implant unit to the size of the chamber at a position between said second portion of the chamber and said lens and immobilize the implant unit in the chamber.

2. The intraocular implant unit of claim 1 wherein said means extending from said limb includes:
an arcuate rim centered on the end of said limb, said rim conforming to a circle having a diameter substantially equal to the diameter of the circularly bounded chamber of the patient's eye.

3. The intraocular implant unit of claim 2 wherein said lens is of the same material as said limb, said arcuate rim and said flexible strand.

4. The intraocular implant unit of claim 2 wherein said lens, said limb, said arcuate rim and said flexible strand are made of material of the nature of polymethylmetharcrylate.

5. The intraocular implant unit of claim 1 wherein said limb is disposed in a 6-o'clock position along the margin of said lens.

6. The intraocular implant unit of claim 1 wherein said flexible strand and said lens are integrally formed.

7. The intraocular implant unit of claim 1 wherein said lens and said flexible strand are composed of a material of the nature of polymethylmethacrylate.

8. The intraocular implant unit of claim 1 wherein said limb is substantially rigid.

* * * * *